United States Patent
Shie et al.

(10) Patent No.: US 9,750,450 B2
(45) Date of Patent: Sep. 5, 2017

(54) METHOD, ELECTRONIC APPARATUS, AND COMPUTER READABLE MEDIUM OF CONSTRUCTING CLASSIFIER FOR SKIN-INFECTION DETECTION

(71) Applicant: HTC Corporation, Taoyuan (TW)

(72) Inventors: Chuen-Kai Shie, Taoyuan (TW); Chung-Hsiang Chuang, Taoyuan (TW); Chun-Nan Chou, Taoyuan (TW); Meng-Hsi Wu, Taoyuan (TW); Edward Chang, Taoyuan (TW)

(73) Assignee: HTC Corporation, Taoyuan (TW)

( * ) Notice: Subject to any disclaimer, the term of this patent is extended or adjusted under 35 U.S.C. 154(b) by 55 days.

(21) Appl. No.: 14/857,820

(22) Filed: Sep. 18, 2015

(65) Prior Publication Data
US 2017/0083793 A1    Mar. 23, 2017

(51) Int. Cl.
*G06K 9/00*    (2006.01)
*A61B 5/00*    (2006.01)
*G06T 7/00*    (2017.01)
*G06K 9/62*    (2006.01)

(52) U.S. Cl.
CPC .............. *A61B 5/444* (2013.01); *G06K 9/627* (2013.01); *G06K 9/628* (2013.01); *G06K 9/6255* (2013.01); *G06T 7/0014* (2013.01); *G06T 7/0083* (2013.01); *G06T 2207/20081* (2013.01); *G06T 2207/20112* (2013.01); *G06T 2207/30088* (2013.01)

(58) Field of Classification Search
None
See application file for complete search history.

(56) References Cited

U.S. PATENT DOCUMENTS

| | | | | |
|---|---|---|---|---|
| 5,016,173 A  * | 5/1991 | Kenet | ......... | A61B 5/0059 382/128 |
| 6,571,003 B1 * | 5/2003 | Hillebrand | ........... | A61B 5/0064 382/100 |
| 6,937,749 B2 * | 8/2005 | Garnier | ............... | A61B 5/442 382/128 |
| 7,454,046 B2 * | 11/2008 | Chhibber | ............... | A61B 5/442 382/118 |

(Continued)

OTHER PUBLICATIONS

F. Ercal, A. Chawla, W. V. Stoecker, Hsi-Chieh Lee and R. H. Moss, "Neural network diagnosis of malignant melanoma from color images," in IEEE Transactions on Biomedical Engineering, vol. 41, No. 9, pp. 837-845, Sep. 1994.*

(Continued)

*Primary Examiner* — Andrae S Allison
(74) *Attorney, Agent, or Firm* — Jianq Chyun IP Office

(57) ABSTRACT

The disclosure provides a method, an electronic apparatus, and a computer readable medium of constructing a classifier for skin-infection detection. The method includes the following steps. A codebook of representative features is constructed based on a plurality of target-disease-irrelevant images. Transfer-learned disease features are extracted from target-disease images according to the codebook without any medical domain knowledge, where the target-disease images are captured by at least one image capturing device. Supervised learning is performed based on the transfer-learned target-disease features to train the classifier for skin-infection detection.

14 Claims, 2 Drawing Sheets

(56) References Cited

U.S. PATENT DOCUMENTS

| | | | | |
|---|---|---|---|---|
| 8,131,029 | B2* | 3/2012 | Chhibber | G06K 9/00288 |
| | | | | 382/118 |
| 8,290,257 | B2* | 10/2012 | Demirli | A61B 5/441 |
| | | | | 382/128 |
| 8,401,300 | B2* | 3/2013 | Jiang | A61B 5/442 |
| | | | | 382/128 |
| 8,433,116 | B2* | 4/2013 | Butler | G06F 19/321 |
| | | | | 382/128 |
| 8,452,063 | B2* | 5/2013 | Wojton | A61B 5/444 |
| | | | | 382/128 |
| 8,731,248 | B2* | 5/2014 | Li | G06K 9/00281 |
| | | | | 382/117 |
| 2016/0358085 | A1* | 12/2016 | Abadi | G06N 99/005 |

OTHER PUBLICATIONS

Marin et al, Detection of melanoma through image recognition and artificial neural networks, D.A. Jaffray (ed.), World Congress on Medical Physics and Biomedical Engineering, Jun. 7-12, 2015, Toronto, Canada.*

Cheerla et al, Automatic Melanoma Detection Using Multi-Stage Neural Networks, International Journal of Innovative Research in Science, Engineering and Technology, vol. 3, Issue 2, Feb. 2014.*

Andrews et al , Transfer Representation-Learning for Anomaly Detection, Proceedings of the 33 rd International Conference on Machine Learning, New York, NY, USA, 2016.*

Oquab, M., Bottou, L., Laptev, I., and Sivic, J. Learning and transferring mid-level image representations using convolutional neural networks. In Proceedings of the IEEE Conference on Computer Vision and Pattern Recognition, pp. 1717-1724, 2014.*

Shie et al., "A hybrid feature-based segmentation and classification system for the computer aided self-diagnosis of otitis media," 36th Annual International Conference of the IEEE Engineering in Medicine and Biology Society (EMBC), Aug. 26-30, 2014, pp. 1-4.

Shie et al., "Transfer Representation Learning for Medical Image Analysis," retrieved from http://infolab.stanford.edu/~echang/ HTC_OM_Final.pdf, downloaded on Sep. 17, 2015, pp. 1-4.

* cited by examiner

METHOD, ELECTRONIC APPARATUS, AND COMPUTER READABLE MEDIUM OF CONSTRUCTING CLASSIFIER FOR SKIN-INFECTION DETECTION

TECHNICAL FIELD

The disclosure relates to a method, an electronic apparatus, and a computer readable medium of constructing a classifier for skin-infection detection.

BACKGROUND

Traditional image-based skin-infection (e.g., Melanoma, Ringwork, Otitis Media, and Otitis External) detections or diagnoses require domain expertise. Skin-infection features derived from heuristics are extracted from images for conducting classification and analysis. For example, Dermatologists have developed "ABCDE" rules to help diagnose melanoma, which is the most serious type of skin cancer. Such rules are fundamentally based on the measures of size, shape and color. Otitis media (OM) detection is another good example of image-based inner-ear skin-infection diagnosis. Prominent symptoms of OM include skin inflammation, redness, bulging and a perforation of the middle ear. However, specifying such kind of human heuristic features involves a hand-crafted process, and thereby requires domain expertise. Often times, human heuristics obtained from domain experts may not be able to capture the most discriminative characteristics, and hence the extracted features cannot achieve high detection accuracy. Besides the problem of feature representation, developing a disease-diagnosis classifier also faces the challenge of limited amount of labeled training data. Under such constraint, even an effective model may fail to learn discriminative features. Inevitably, the lack of labeled data is a common issue for almost all medical analysis.

SUMMARY OF THE DISCLOSURE

Accordingly, the disclosure is directed to a method, an electronic apparatus, and a computer readable medium of constructing a classifier for skin-infection detection using images, which provides an approach to construct a robust classifier with high classification accuracy.

According to one of the exemplary embodiments, the disclosure is directed to a method of constructing a classifier for skin-infection detection using images. The method would include at least but not limited to the following steps. A codebook of representative features is constructed based on a plurality of target-disease-irrelevant images. Transfer-learned features are then extracted from target-disease images according to the codebook, where the target disease images are captured by at least one image capturing device. Supervised learning is performed based on the transfer-learned target-disease features to train the classifier for skin-infection detection.

According to one of the exemplary embodiments, the disclosure is directed to an electronic apparatus. The electronic apparatus would at least, but not limited to, a storage unit, a communication interface, and one or more processing units, where the processing unit is coupled to the storage unit and the communication interface. The storage unit is configured to record modules, and the processing unit is configured to access and execute the modules recorded in the storage unit. The modules include a codebook constructing module, a feature extracting module, and a classifier training module. The codebook construction module constructs a codebook of representative features based on target-disease-irrelevant images obtained via the communication interface. The feature extracting module extracts transfer-learned target-disease features from target-disease images obtained via the communication interface according to the codebook, where the target-disease images are captured by at least one image capturing device. The classifier training module performs supervised learning based on the transfer-learned target-disease features to train the classifier for skin-infection detection.

According to one of exemplary embodiments, the disclosure is also directed to a non-transitory computer readable medium, which records computer program to be loaded into an electronic apparatus to execute the steps of the aforementioned method of constructing a classifier for skin-infection detection. The computer program is composed of a plurality of program instructions (for example, an organization chart, establishing program instruction, a table approving program instruction, a setting program instruction, and a deployment program instruction, etc), and these program instructions are loaded into the electronic apparatus and executed by the same to accomplish various steps of the method of constructing a classifier for skin-infection detection.

In view of the aforementioned descriptions, while the amount of labeled disease images for conducting statistical analysis is limited, a codebook of representative features is constructed based on target-disease-irrelevant images in the disclosure. Transfer-learned target-disease features are extracted from target-disease images according to the codebook, and the classifier for skin-infection detection is trained by performing supervised learning based on the transfer-learned target-disease features. The disclosure not only mitigates the lack of labeled data problem and remedies the lack of domain knowledge to extract features, but also provides an approach to construct a robust classifier for skin-infection detection with high classification accuracy.

In order to make the aforementioned features and advantages of the present disclosure comprehensible, preferred embodiments accompanied with figures are described in detail below. It is to be understood that both the foregoing general description and the following detailed description are exemplary, and are intended to provide further explanation of the disclosure as claimed.

It should be understood, however, that this summary may not contain all of the aspect and embodiments of the present disclosure and is therefore not meant to be limiting or restrictive in any manner. Also the present disclosure would include improvements and modifications, which are obvious to one skilled in the art.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

Figure 1:
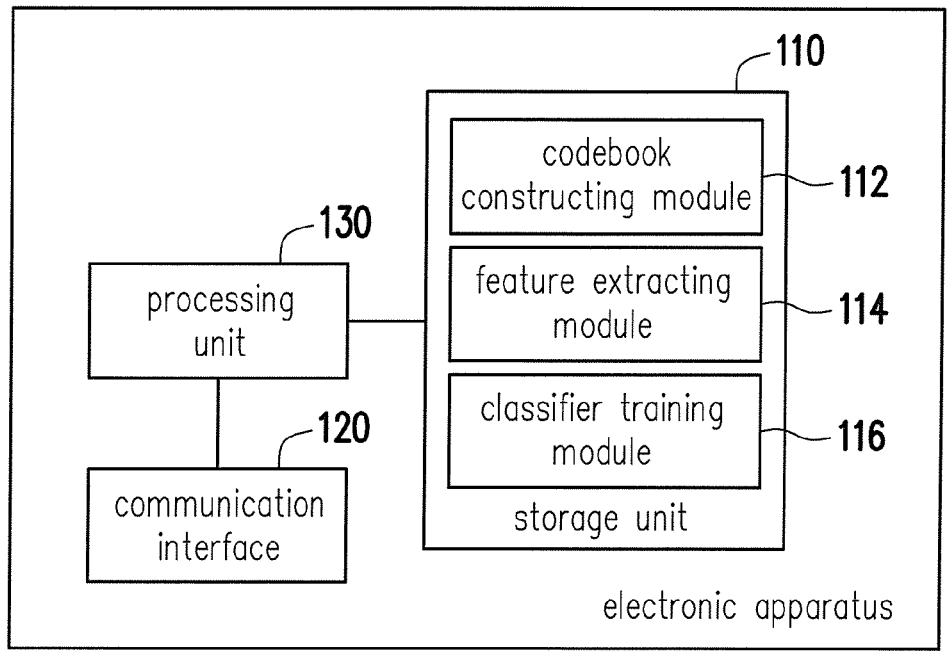
FIG. 1 illustrates a schematic diagram of a proposed electronic apparatus of constructing a classifier for skin-infection detection in accordance with one of the exemplary embodiments of the disclosure.

To make the above features and advantages of the application more comprehensible, several embodiments accompanied with drawings are described in detail as follows.

DESCRIPTION OF THE EMBODIMENTS

There are two major challenges to overcome when developing a classifier to perform automatic disease diagnosis. First, the amount of labeled medical data is typically very limited, and a classifier cannot be effectively trained to attain high disease-detection accuracy. Second, medical domain knowledge is required to identify representative features in data for detecting a target disease. Most computer scientists and statisticians do not have such domain knowledge. The main concept of the disclosure is to develop disease classifiers by adopting transfer learning. Transfer learning is defined as the ability of a system to recognize and apply knowledge and skills learned in previous tasks to a novel task. By leveraging such concept, the issues of labeled data scarcity and medical domain knowledge shortage would be solved.

Some embodiments of the disclosure will now be described more fully hereinafter with reference to the accompanying drawings, in which some, but not all embodiments of the application are shown. Indeed, various embodiments of the disclosure may be embodied in many different forms and should not be construed as limited to the embodiments set forth herein; rather, these embodiments are provided so that this disclosure will satisfy applicable legal requirements. Like reference numerals refer to like elements throughout.

FIG. 1 illustrates a schematic diagram of a proposed electronic apparatus of constructing a classifier for skin-infection detection in accordance with one of the exemplary embodiments of the disclosure. All components of the electronic apparatus and their configurations are first introduced in FIG. 1. The functionalities of the components are disclosed in more detail in conjunction with FIG. 2.

Referring to FIG. 1, an exemplary electronic apparatus 100 would include a storage unit 110, a communication interface 120, and one or more processing units 130, where the processing unit 130 is coupled to the storage unit 110 and the communication interface 120. The electronic apparatus 100 may be a personal computer, a laptop computer, a server computer, a tabular computer, a smart phone, a workstation, or other types of computing apparatuses or platforms.

The storage unit 110 may be one or a combination of a stationary or mobile random access memory (RAM), a read-only memory (ROM), a flash memory, a hard drive or other various forms of non-transitory, volatile, and non-volatile memories. The storage unit 110 is configured to record a plurality of modules executable by the processing unit 130. The modules include a codebook constructing module 112, a feature extracting module 114, and a classifier training module 116. The modules may be loaded into the processing unit 130 for constructing a classifier for skin-infection detection.

The communication interface 120 may be an Ethernet card, an RS-232 port, a USB port, an 802.11 card, a 3G wireless modem, a 4G wireless modem, or other wired and wireless interfaces and technologies known to the person skilled in the art. The communication interface 120 allows the electronic apparatus 100 to exchange data with external devices.

The processing unit 130 may be, for example, a central processing unit (CPU) or other programmable devices for general purpose or special purpose such as a microprocessor, a digital signal processor (DSP), a graphical processing unit (GPU), a programmable controller, an application specific integrated circuit (ASIC), a programmable logic device (PLD) or other similar or a combination of aforementioned components. The processing unit 130 is capable of accessing and executing the modules recorded in the storage unit 110 and would be used to perform the method of constructing a classifier for skin-infection detection as proposed.

Figure 2:
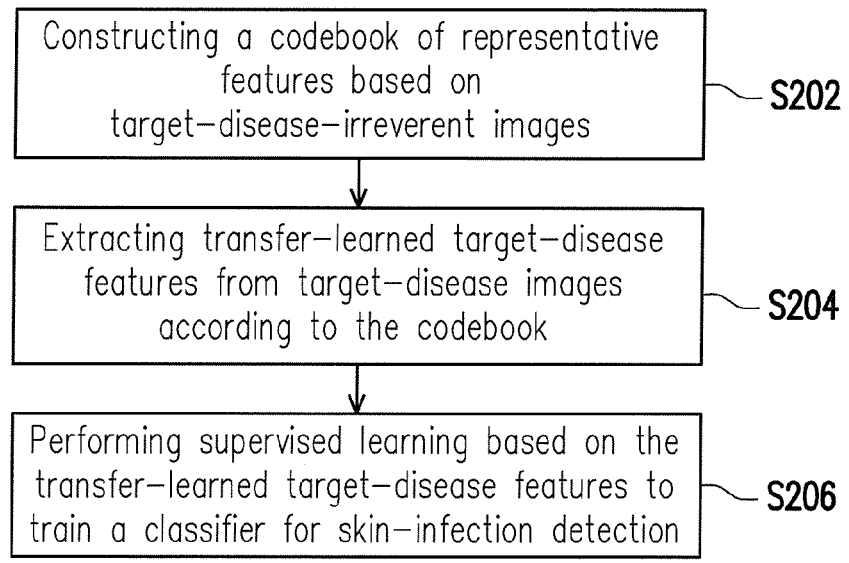
FIG. 2 illustrates a flowchart of a method of constructing a classifier for skin-infection detection in accordance with one of the exemplary embodiments of the disclosure.

FIG. 2 illustrates a flowchart of a method of constructing a classifier for skin-infection detection in accordance with one of the exemplary embodiments of the disclosure. The steps of FIG. 2 could be implemented by the proposed electronic apparatus 100 as illustrated in FIG. 1.

Referring to FIG. 2, the codebook constructing module 112 of the electronic apparatus 100 constructs a codebook of representative features based on target-disease-irreverent images obtained via the communication interface 120 (Step S202). Herein, the target-disease-irreverent images refer to images irreverent to skin infection associated with a classifier to be constructed. In detail, while the amount of labeled medical images for conducting statistical analysis is typically limited, the codebook constructing module 112 would perform representation learning, e.g., deep learning, on an entirely irrelevant image dataset which is typically very large in volume to be effective. For example, the codebook constructing module 112 may obtain the target-disease-irrelevant images from ImageNet, which is the largest image database provided with 15 million labeled high-resolution images in over 22,000 categories of daily objects. In other examples, the codebook constructing module 112 may also obtain the target-disease-irreverent images from other image sources. The codebook constructing module 112 would construct the codebook based on such large target-disease-irrelevant image dataset and representation learning methods with absolutely no medical domain knowledge. In other words, no domain expert is involved in identifying any features for the target-disease detection at this stage.

In machine learning, representation learning refers to a set of techniques that learn useful features or representations from the transformation of input raw data that can be easily utilized in building classifiers or other predictors. It deals with how to represent an image or patches in the image as numerical vectors, which are known as feature descriptors. The feature descriptors would possess the ability to deal with image transformations such as intensity, rotation, scale, and affine variations to some extent. In one exemplary embodiment, the codebook constructing module 112 would learn the feature representation of the target-disease-irrelevant images by leveraging a neural-network-based approach or an energy-based approach. The models used in the neural-network-based approach and the energy-based approach would be referred to as "a first representation learning model" and "a second representation learning model" respectively.

In one neural-network-based approach, a deep convolutional neural network (CNN) model which achieves remarkable improvement in classifying images, audio, and speech data may be utilized as the first representation learning model. For example, AlexNet, a variant of deep CNN model, may be used. AlexNet contains eight layers of neurons, where the first five layers are convolutional, and the remaining three layers are fully-connected. Different layers would represent different levels of abstraction concepts. An autoencoder which automatically learns features from unlabelled data may be used in another neural-network-based approach. For example, the sparse autoencoder, which is a variant of autoencoder and imposes sparsity constraints during the learning process, may be used. The sparsity constraint is typically set to a small value close to zero. In other words, the average activation of each hidden neuron is nearly zero. An energy-based approach may exploit a Restricted Boltzmann machine (RBM), which can learn a probability distribution over its set of inputs. For example, a deep belief network, which stacks multiple RBMs or autoencoders and trains the stacked RBMs or autoencoders in a greedy manner, may be used as the second representation learning model. That is, the second representation learning model would include at least one hidden layer having multiple hidden units. The activations values of stacked autoencoders of the inner layers in the first representation learning model or the probabilistic values of the hidden units in the second representation learning model can be used as the representative features of the input data (i.e. target-disease-irrelevant images).

Next, the feature extracting module 114 of the electronic apparatus 100 extracts transfer-learned disease features from target-disease images obtained via the communication interface 120 according to the codebook (Step S204). In detail, each of the target-disease images is an image captured by an image capturing device and performed diagnosis of disease by professionals. Such image capturing device could be an instrument for disease examination such as an otoscope, a demioscopy, a fundoscopy, a laryngoscope, and so forth. The feature extracting module 114 may obtain the target-disease images from one or more databases of a clinical system, from the internet, directly from one or more medical image capturing devices, or any other sources as long as the obtained images have been diagnosed and labeled. In other words, the target-disease images are considered as labeled data and are directly associated with the classifier to be constructed. For example, if the classifier is used for Otitis Media (OM) detection, the target-disease images would be OM images captured by otoscopes. The feature extracting module 114 would use the learned features from a large amount of the target-disease-irrelevant images to describe the target-disease images. Hence, the feature extracting module 114 would be considered as an encoder which captures generic features (i.e. the transfer-learned target-disease features) of the target-disease images in a vector form by referencing the codebook.

In an exemplary embodiment in which the codebook is constructed based on a neural network, each target-disease image is first input to the first representation learning model. The information of each target-disease image such as its representations and features would propagate through the layers (i.e. from an input layer to an output layer through inner layers). Each layer is a weighted combination of the previous layer and stands for a feature representation of the input the target-disease image. Since the computation is hierarchical, higher layers intuitively represent high abstraction concepts. For images, the neurons from lower levels describe rudimental perceptual elements such as edges and corners, while higher layers represent object parts such as contours and categories. For example, in terms of the AlexNet, the feature extracting module 114 would extract transfer-learned features of the images from the fifth, sixth, and seventh layers (conventionally denoted as pool5, fc6, and fc7 respectively) to capture higher-level abstractions. The transfer-learned features would not be extracted from the eighth layer is because it only produces the probability of the class prediction, which is not a representation of a target-disease image. In an exemplary embodiment in which the codebook is constructed based on a deep belief network, the feature extracting module 114 would extract transfer-learned features of the images in a similar fashion.

To further improve the classification accuracy, especially for skin-infection image classification whose images are often with noise, image segmentation could be utilized as an image pre-preprocessing step prior to feature extraction. To be specific, the feature extracting module 114 may first segment a target region from each of the target-disease images to correspondingly generate a segmented target-disease image, and extract the transfer-learned target-disease features from the segmented target-disease images thereafter.

Although there exists various image segmentation techniques such as threshold, region growing, and edge-detection, such color and position based techniques are not reliable due to the complexity of skin-infection images. A powerful active contour segmentation technique which minimizes an energy function by evolving an active contour from an initial position towards a desired boundary would be applied to each of the target-disease images. Take melanoma as an example, image segmentation is difficult to be performed on nevus in a melanoma image due to its colorfulness and fuzzy edges. A robust image segmentation method based on an active contour technique is proposed as follows. A contour located at the center of skin region in a target-disease image (i.e. a melanoma image) is initialized, where the contour could be identified according to the color of human skin. Next, the contour evolves to minimize a predefined energy function and finally terminates at a desired boundary (referred to as a terminated boundary). In such instance, the feature extracting module 114 could segment the target region from the target-disease image according to the terminated boundary to generate a segmented target-disease image.

Take OM as another example, to segment an eardrum region an OM image is suggested since the visual cues of OM mainly appear on an eardrum. There are two obstacles for accurate performance by such approach. First, an initial curve position is required and yet it is difficult to obtain from an OM image where an eardrum is centrally located. Second, reflected light makes the color of an ear canal close to bright white and inadvertently forces the curves to evolve to an incorrect position. To solve the obstacles addressed above, the segmentation method would remove a bright ear canal region from an OM image in the first iteration and segment the desired eardrum region close to a circle or ellipse in shape in the second iteration. However, if there is no bright ear canal region in the OM image, then segmentation method would not perform the first iteration. By applying such segmentation technique, the segmentation method is able to segment the eardrum region not centered locally without user guidance.

More technically speaking, whether any unwanted region such as a bright ear canal region as addressed above exists in a target-disease image would be first determined. If yes, the unwanted region would be removed from the OM image to generate a first processed image. If no, the target-disease image would be directly set as the first processed image without any removal process being involved. Next, the target-disease region would be segmented out in a pre-defined shape (e.g. a circular or elliptical shape) from the first processed image to generate a segmented target-disease image. In such instance, the feature extracting module 114 could segment the target region from the target-disease image to generate a segmented target-disease image.

Once the feature extracting module 114 has extracted the transfer-learned target-disease features, the classifier training module 116 performs supervised learning based on the transfer-learned target-disease features to train the classifier for skin-infection detection (Step S206). In other words, the classifier training module 116 would employ supervised learning with disease labels and transfer-learned disease features instead of raw disease features. In machine learning, supervised learning refers to inferring a model from labeled data, and the inferred model can predict answers of unseen data. In an exemplary embodiment, the classifier training module 116 may employ a Support Vector Machine (SVM) classifier as the classifier for disease detection, where the SVM classifier is considered as an effective supervised learning tool used in classification. After the classifier for skin-infection detection is constructed, in one scenario where a personal dermoscopy is available, preliminary diagnosis could be able to be performed at home, and medical attention could be sought. For instance, the classifier for melanoma detection could be installed in the dermoscopy. After a new skin image is captured by the dermoscopy, the installed classifier would classify whether the new skin image corresponds to any nevi conditions, and the dermoscopy would output the classification result by, for example, a display. In another instance, the classifier for melanoma detection could be installed in a cloud server or an external electronic apparatus, the dermoscopy would transmit the new skin image to the classifier and receive the classification result from the classifier via wired or wireless transmission. In another instance, the new skin image along with the classification result may be transmitted to the medical database. Similar scenario could also apply to other medical image capturing devices.

Figure 3:
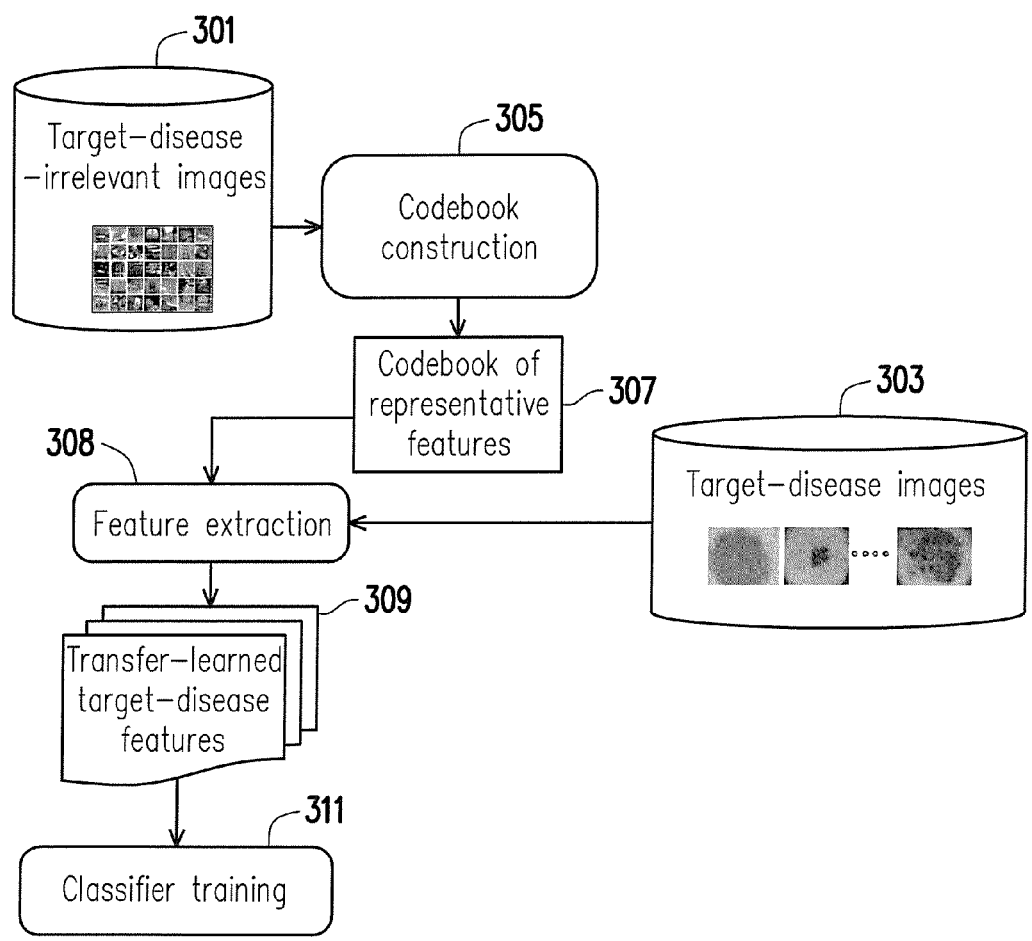
FIG. 3 illustrates a functional block diagram of a method of constructing a classifier for skin-infection detection in accordance with one of the exemplary embodiments of the disclosure.

The proposed method of constructing a classifier for skin-infection detection could be summarized by FIG. 3 in terms of functional block diagrams in accordance with one of the exemplary embodiments of the disclosure.

Referring to FIG. 3, codebook construction 305 using representation learning methods is performed to generate a codebook of representative features 307 based on a large amount of disease-irrelevant images 301. Feature extraction 308 is performed on disease images 303 to obtain transfer-learned disease features 309. The classifier training 311 is performed based on the transfer-learned disease features.

In an experiment with melanoma-irrelevant images obtained from ImageNet and merely 200 dermoscopy images from $PH^2$ database (http://www.fc.up.pt/addi/ph2%20database.html), the melanoma detection accuracy of the classifier constructed purely based on transfer-learned melanoma feature are 89.06%, 85.31% and 79.38% when the transfer-learned features are extracted from the fifth layer (pool5), the sixth layer (fc6), and the seventh layer (fc7) of the AlexNet respectively. Human heuristic method based on "ABCD" rule has a similar performance, which achieves 89.06% in accuracy. However, this approach requires developers to possess domain knowledge about skin infections prior to encoding the knowledge into mathematical expressions and computer algorithms.

The disclosure also provides a non-transitory computer readable medium, which records computer program to be loaded into an electronic apparatus to execute the steps of the aforementioned method of constructing a classifier for skin-infection detection. The computer program is composed of a plurality of program instructions (for example, an organization chart, establishing program instruction, a table approving program instruction, a setting program instruction, and a deployment program instruction, etc.), and these program instructions are loaded into the electronic apparatus and executed by the same to accomplish various steps of the method aforementioned method of constructing a classifier for skin-infection detection.

In view of the aforementioned descriptions, while the amount of labeled disease images for conducting statistical analysis is limited, a codebook of representative features is constructed based on disease-irrelevant images in the disclosure. Transfer-learned disease features are extracted from disease images according to the codebook, and the classifier for skin-infection detection is trained by performing supervised learning based on the transfer-learned disease features. The disclosure not only mitigates the lack of labeled data problem and remedies the lack of domain knowledge to extract features, but also provides an approach to construct a robust disease classifier with high classification accuracy.

No element, act, or instruction used in the detailed description of disclosed embodiments of the present application should be construed as absolutely critical or essential to the present disclosure unless explicitly described as such. Also, as used herein, each of the indefinite articles "a" and "an" could include more than one item. If only one item is intended, the terms "a single" or similar languages would be used. Furthermore, the terms "any of" followed by a listing of a plurality of items and/or a plurality of categories of items, as used herein, are intended to include "any of", "any combination of", "any multiple of", and/or "any combination of multiples of the items and/or the categories of items, individually or in conjunction with other items and/or other categories of items. Further, as used herein, the term "set" is intended to include any number of items, including zero. Further, as used herein, the term "number" is intended to include any number, including zero.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

Moreover, the claims should not be read as limited to the described order or elements unless stated to that effect. In addition, use of the term "means" in any claim is intended to invoke 35 U.S.C. §112, ¶6, and any claim without the word "means" is not so intended.

What is claimed is:

1. A method of constructing a classifier for melanoma detection comprising:
   constructing a codebook of representative features based on a plurality of target-disease-irrelevant images;
   extracting a plurality of transfer-learned target-disease features from a plurality of target-disease images according to the codebook, wherein the step of extracting the plurality of transfer-learned target-disease features comprises:
   segmenting a target region from each of the target-disease images to correspondingly generate a segmented target-disease image; and
   extracting the transfer-learned target-disease features from the segmented target-disease images; and
   performing supervised learning based on the transfer-learned target-disease features to train the classifier for melanoma detection, wherein the step of segmenting the target region from each of the target-disease images to correspondingly generate the segmented target-disease image comprises:
for each of the target-disease images:
initializing a contour at a center of the target region according to color;
evolving the contour such that a predefined energy function is minimized so as to obtain a terminated boundary; and
segmenting the target region from the target-disease image according to the terminated boundary to generate the segmented target-disease image.

2. A method of constructing a classifier for skin-infection detection comprising:
constructing a codebook of representative features based on a plurality of target-disease-irrelevant images;
extracting a plurality of transfer-learned target-disease features from a plurality of target-disease images according to the codebook, wherein the step of extracting the plurality of transfer-learned target-disease features comprises:
segmenting a target region from each of the target-disease images to correspondingly generate a segmented target-disease image; and
extracting the transfer-learned target-disease features from the segmented target-disease images; and
performing supervised learning based on the transfer-learned target-disease features to train the classifier for skin-infection detection,
wherein the step of segmenting the target region from each of the target-disease images to correspondingly generate the segmented target-disease image comprises:
for each of the target-disease images:
initializing a contour at a center of the target region according to color;
evolving the contour such that a predefined energy function is minimized so as to obtain a terminated boundary; and
segmenting the target region from the target-disease image according to the terminated boundary to generate the segmented target-disease image.

3. The method according to claim 2, wherein the step of constructing the codebook of the representative features based on the target-disease-irrelevant images comprises:
constructing the codebook of the representative features based on the target-disease-irrelevant images by using a first representation learning model, wherein the first representation learning model comprises a plurality of layers of neurons, wherein the layers comprise at least one inner layer, and wherein activation values of the inner layers corresponds to the representative features of the target-disease-irrelevant images.

4. The method according to claim 3, wherein the step of extracting the transfer-learned target-disease features from the target-disease images according to the codebook comprises:
for each of the target-disease images:
inputting the target-disease image into the first representation learning model;
propagating information in the target-disease image through the layers; and
obtaining the transfer-learned features of the target-disease image according to at least one of the inner layers.

5. The method according to claim 2, wherein the step of constructing the codebook of the representative features based on the target-disease-irrelevant images comprises:
constructing the codebook of the representative features based on the target-disease-irrelevant images by using a second representation learning model, wherein the second representation learning model comprises a plurality of layers of units, wherein the layers comprise at least one hidden layer having a plurality of hidden units, and wherein probabilistic values of the hidden units correspond to the representative features of the target-disease-irrelevant images.

6. The method according to claim 5, wherein the step of extracting the transfer-learned features from the target-disease images according to the codebook comprises:
for each of the target-disease images:
inputting the target-disease image into the second representation learning model;
propagating information in the target-disease image through the layers; and
obtaining the transfer-learned features of the target-disease image according to at least one of the hidden units.

7. The method according to claim 2, wherein after the step of performing supervised learning on at least the transfer-learned features to train the classifier for skin-infection detection, the method further comprises:
capturing a new image by an image capturing device; and
classifying whether the new image corresponds to a skin infection condition by using the classifier for skin-infection detection to generate a classification result; and
outputting the classification result.

8. An electronic apparatus comprising:
a communication interface;
a memory, recording a plurality of modules; and
one or a plurality of processors, coupled to the communication interface and the memory, and accessing and executing the modules stored in the memory, wherein the modules comprise:
a codebook constructing module, constructing a codebook of representative features based on a plurality of target-disease-irrelevant images obtained via the communication interface;
a feature extracting module, extracting a plurality of transfer-learned target-disease features from a plurality of target-disease images obtained via the communication interface according to the codebook, wherein the feature extracting module segments a target region from each of the target-disease images to correspondingly generate a segmented target-disease image, and extracts the transfer-learned target-disease features from the segmented target-disease images; and
a classifier training module, performing supervised learning based on the transfer-learned target-disease features to train the classifier for skin-infection detection,
wherein for each of the target-disease images, the feature extracting module initializes a contour at a center of the target region according to color, evolves the contour such that the energy function is minimized so as to obtain a terminated boundary, and segments the target region from the target-disease image according to the terminated boundary to generate the segmented target-disease image.

9. The electronic apparatus according to claim 8, wherein the codebook constructing module constructs the codebook based on the target-disease-irrelevant images by using a first representation learning model, wherein the first representation learning model comprises a plurality of layers of neurons, wherein the layers comprise at least one inner layer, and wherein activation values of the inner layers corresponds to the representative features of the target-disease-irrelevant images.

10. The electronic apparatus according to claim 9, wherein for each of the target-disease images, the feature extracting module inputs the target-disease image into the first representation learning model, propagates information in the target-disease image through the layers, and obtains the transfer-learned features of the target-disease image according to at least one of the inner layers.

11. The electronic apparatus according to claim 9, wherein the classifier obtains a new image captured by an image capturing device via the communication interface, classifies whether the new image corresponds to a skin infection condition to generate a classification result, and outputs the classification result.

12. The electronic apparatus according to claim 8, wherein the codebook constructing module constructs the codebook based on the target-disease-irrelevant images by using a second representation learning model, wherein the second representation learning model comprises a plurality of layers of units, wherein the layers comprise at least one hidden layer having a plurality of hidden units, and wherein probabilistic values of the hidden units correspond to the representative features of the target-disease-irrelevant images.

13. The electronic apparatus according to claim 12, wherein for each of the target-disease images, the feature extracting module inputs the target-disease image into the second representation learning model, propagates information in the target-disease image through the layers, and obtains the transfer-learned features of the target-disease image according to at least one of the hidden units.

14. A non-transitory computer readable medium, storing programs to be loaded into an electronic apparatus to perform steps of:
    constructing a codebook of representative features based on a plurality of target-disease-irrelevant images;
    extracting a plurality of transfer-learned target-disease features from a plurality of target-disease images according to the codebook, wherein the step of extracting the plurality of transfer-learned target-disease features comprises:
        segmenting a target region from each of the target-disease images to correspondingly generate a segmented target-disease image; and
        extracting the transfer-learned target-disease features from the segmented target-disease images;
    performing supervised learning based on the transfer-learned target-disease features to train the classifier for skin-infection detection,
    wherein the step of segmenting the target region from each of the target-disease images to correspondingly generate the segmented target-disease image comprises:
    for each of the target-disease images:
        initializing a contour at a center of the target region according to color;
        evolving the contour such that a predefined energy function is minimized so as to obtain a terminated boundary; and
        segmenting the target region from the target-disease image according to the terminated boundary to generate the segmented target-disease image.

* * * * *